(12) United States Patent
Hart et al.

(10) Patent No.: US 8,321,140 B2
(45) Date of Patent: Nov. 27, 2012

(54) QUANTIFICATION OF NUCLEIC ACID MOLECULES USING MULTIPLEX PCR

(75) Inventors: Kyle Hart, Belmont, MA (US); Vladimir Dancik, North Andover, MA (US); Michael Bristol, Foxboro, MA (US); Patrick Wells, North Attleboro, MA (US); Elizabeth Garcia, Barrington, RI (US); Vladimir Slepnev, Newton, MA (US); John Unger, Norwood, MA (US)

(73) Assignee: Primeradx, Inc., Mansfield, MA (US)

( * ) Notice: Subject to any disclaimer, the term of this patent is extended or adjusted under 35 U.S.C. 154(b) by 675 days.

(21) Appl. No.: 12/266,133

(22) Filed: Nov. 6, 2008

(65) Prior Publication Data

US 2009/0136951 A1    May 28, 2009

Related U.S. Application Data

(60) Provisional application No. 61/002,149, filed on Nov. 7, 2007.

(51) Int. Cl.
*G06F 19/20* (2011.01)
(52) U.S. Cl. ......................................................... 702/19
(58) Field of Classification Search .......................... None
See application file for complete search history.

(56) References Cited

FOREIGN PATENT DOCUMENTS

| | | |
|---|---|---|
| EP | 1798542 A | 6/2007 |
| EP | 1804172 A | 7/2007 |
| WO | 03/073233 A | 9/2003 |
| WO | 2005/030990 A | 4/2005 |
| WO | 2006/014464 A | 2/2006 |
| WO | 2006/085964 A | 8/2006 |
| WO | 2007/002316 A | 1/2007 |

OTHER PUBLICATIONS

Garcia, E. P., Dowding, L. A., Stanton, L. W. & Slepnev, V. I. Scalable transcriptional analysis routine-multiplexed quantitative real-time polymerase chain reaction platform for gene expression analysis and molecular diagnostics. The Journal of molecular diagnostics 7, 444-454 (2005).*
Gibson, U. E., Heid, C. A. & Williams, P. M. A novel method for real time quantitative RT-PCR. Genome Research 6, 995-1001 (1996).*
Li, X. & Wang, X. Application of real-time polymerase chain reaction for the quantitation of interleukin-1β mRNA upregulation in brain ischemic tolerance. Brain Research Protocols 5, 211-217 (2000).*
Gevertz, J. L., Dunn, S. M. & Roth, C. M. Mathematical model of real-time PCR kinetics. Biotechnol. Bioeng. 92, 346-355 (2005).*
Rebrikov, D., Trofimov, D., Rebrikov, D. V. & Trofimov. Real-time PCR: A review of approaches to data analysis. Applied Biochemistry and Microbiology 42, 455-463 (2006).*
Woolley, A. T. et al. Functional integration of PCR amplification and capillary electrophoresis in a microfabricated DNA analysis device. Anal. Chem. 68, 4081-4086 (1996).*

\* cited by examiner

*Primary Examiner* — Marjorie Moran
*Assistant Examiner* — Soren Harward
(74) *Attorney, Agent, or Firm* — Mark J. FitzGerald; Nixon Peabody LLP

(57) ABSTRACT

Described are novel quantification methods and systems that permit, within the context of multiplex PCR, the quantification of all targets within a single reaction tube. The methods employ quantitation algorithms applied to the amplification profiles of internal calibration controls or standards utilizing a plurality of nucleic acid templates that are amplified within the same reaction tube as the nucleic acid target(s) interrogated.

6 Claims, 6 Drawing Sheets

Figure 1. Standard curve.
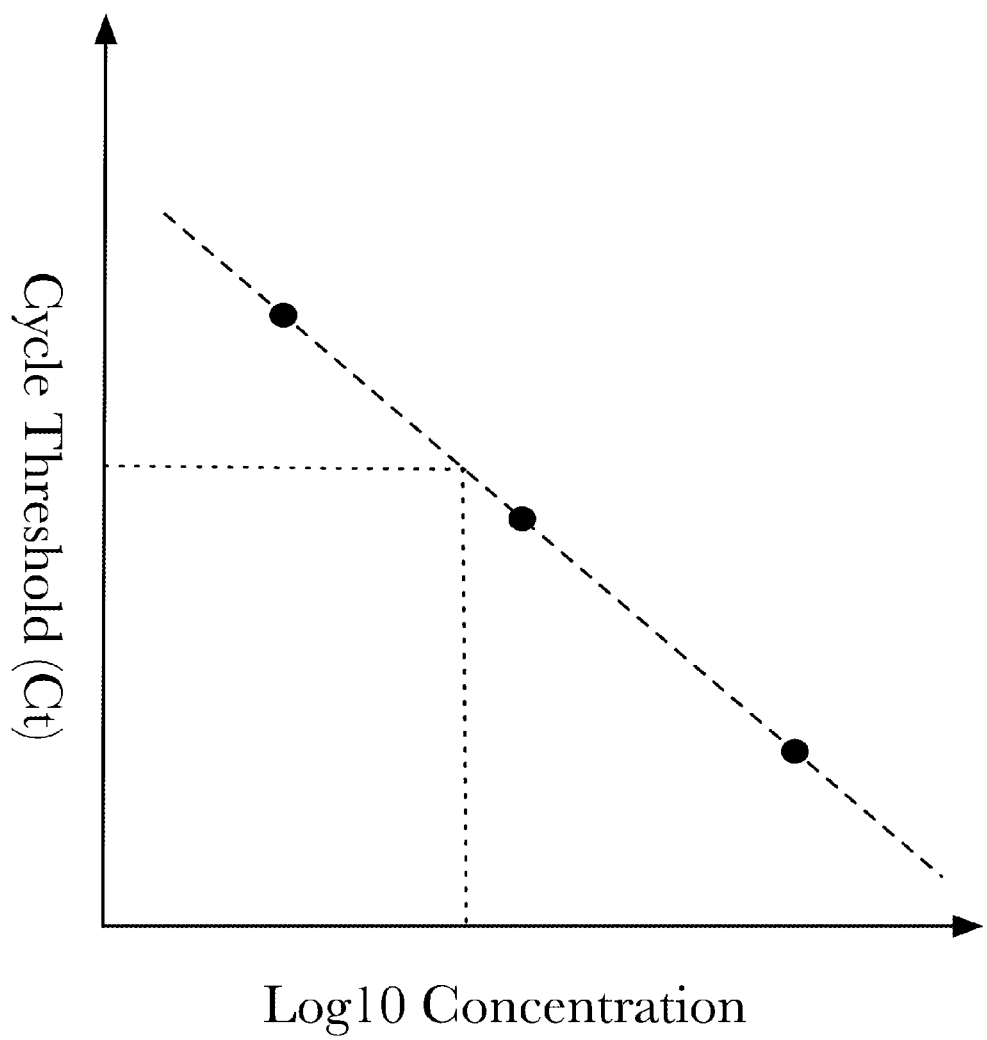

Figure 2. Extending the Standard Curve using Low Concentration Quantification
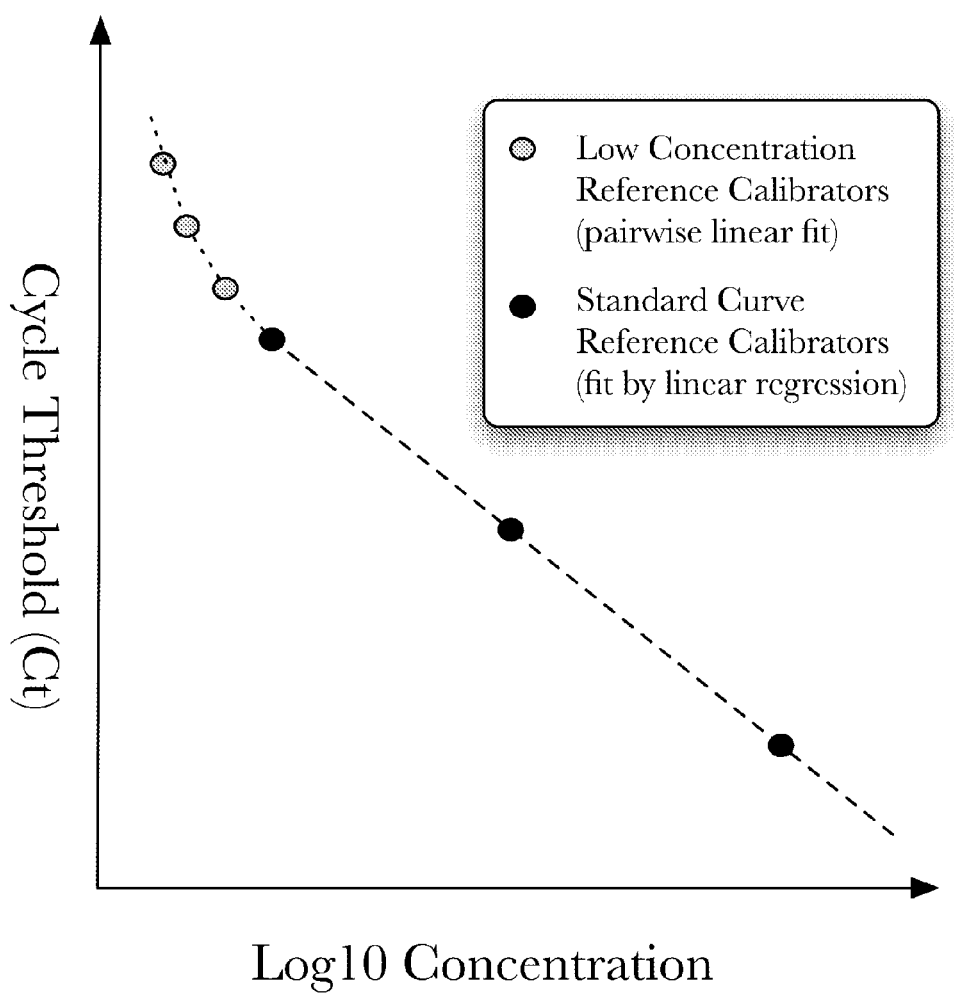

Figure 3: Efficiency of the Quantitative standards:
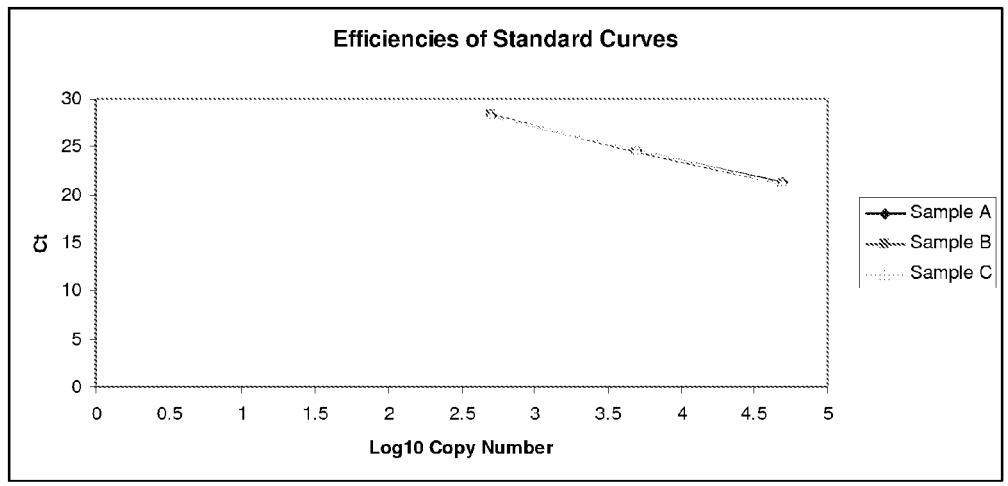
|          | Slope   | R2       | Efficiency  |
|----------|---------|----------|-------------|
| Sample A | -3.4485 | 0.999939 | 1.949759977 |
| Sample B | -3.617  | 0.998294 | 1.890045305 |
| Sample C | -3.5665 | 0.999533 | 1.907159142 |

Figure 4A: Quantification of BK target using log/log Linear plots:
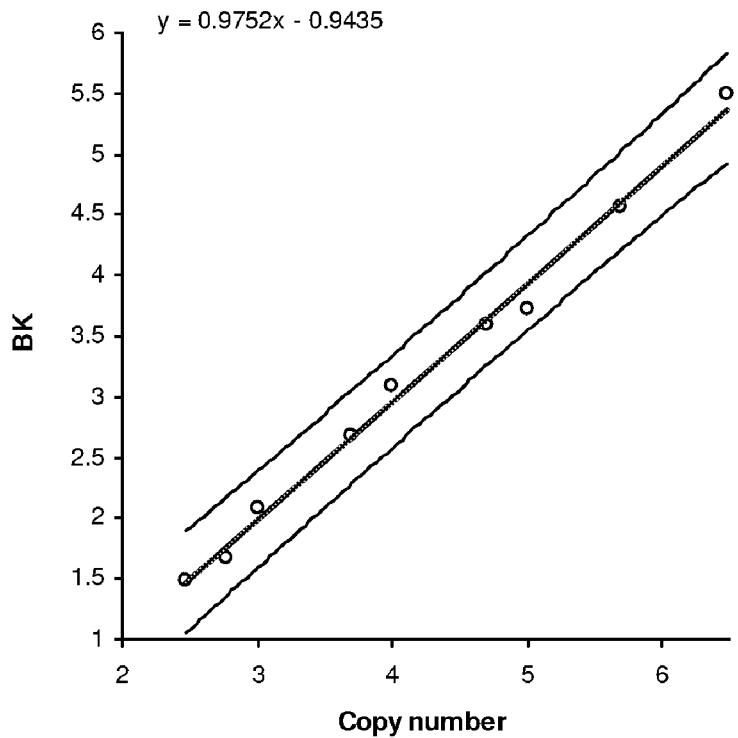
Figure 4B: Quantification of HHV7 target using log/log Linear plots:
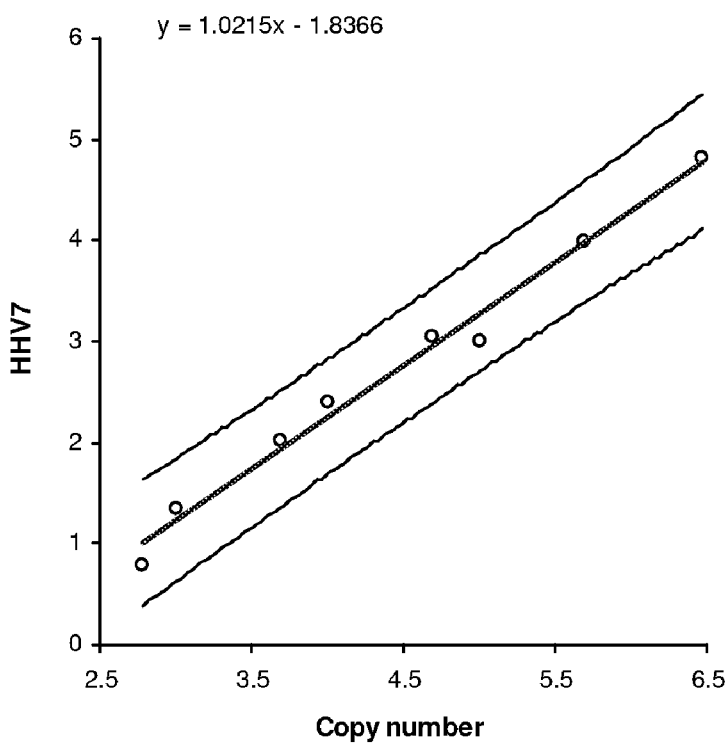

Figure 4C: Quantification of CMV target using log/log Linear plots:
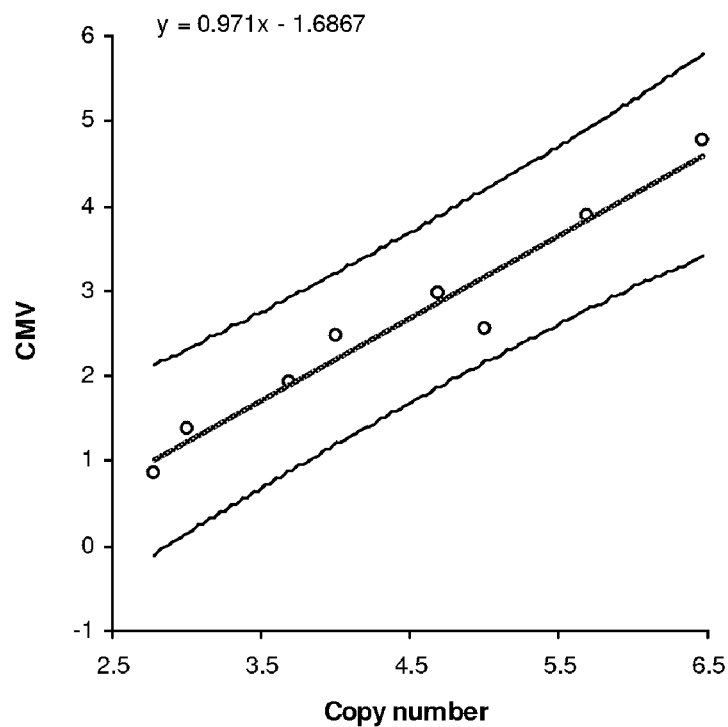

Figure 5: Efficiency of each target in a reaction tube.
|  | Standard 1 | Standard 2 | Standard 3 | BK | HHV7 | CMV | Min - Max Eff Delta |
|---|---|---|---|---|---|---|---|
| Reaction 1 | 1.979 | 1.922 | 1.913 | 1.967 | 1.924 | 1.957 | 0.066 |
| Reaction 2 | 1.989 | 1.969 | 1.941 | 1.944 | 2.000 | 1.950 | 0.059 |
| Reaction 3 | 1.943 | 1.989 | 1.955 | 1.894 | 1.980 | 1.963 | 0.096 |
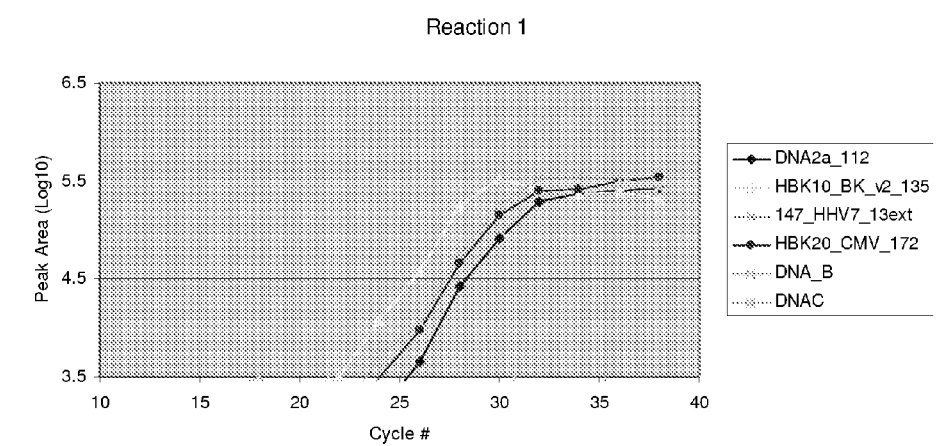

QUANTIFICATION OF NUCLEIC ACID MOLECULES USING MULTIPLEX PCR

CROSS REFERENCE TO RELATED APPLICATIONS

This application claims the benefit under 35 U.S.C. §119 (e) of U.S. Provisional Application No. 61/002,149 filed Nov. 7, 2007, the contents of which are incorporated herein by reference in its entirety.

BACKGROUND OF THE INVENTION

Since the advent of the polymerase chain reaction (PCR) it was recognized that amplification can be used to estimate the initial concentration of a template nucleic acid. However, variations in the efficiency or other aspects of an amplification can and do result from a number of different influences on the reactions. Only if such variations are accounted for or neutralized can one hope to obtain quantitative results. A number of approaches have been used or proposed to address this fundamental issue for quantitative PCR. Multiplex quantitative PCR, or quantitative PCR in which a plurality of target nucleic acids is amplified and quantified in one reaction mixture presents additional challenges.

SUMMARY OF THE INVENTION

Disclosed herein are methods for the determination or estimation of an initial amount of a target nucleic acid, or, preferably, a plurality of different target nucleic acids in a sample. The methods described use a plurality of internal calibration controls, or standards, co-amplified with target nucleic acids. Measurement of signal corresponding to each of the calibration controls at different cycles of a cyclic amplification regimen permits the generation of a standard curve, which is then applied to estimate the initial amount of a target of unknown quantity.

Accordingly, in one aspect, disclosed herein is a method of determining an initial concentration ($Q_0$) of a target nucleic acid template in a sample, the method comprising the steps of: (a) amplifying the target nucleic acid template and a plurality of standard templates, each of the standard templates present at a different, known copy number, in a nucleic acid amplification reaction regimen comprising a plurality of cycles of primer annealing, primer elongation and strand dissociation, wherein the reaction is performed using a reaction mixture comprising the target nucleic acid template and the plurality of standard templates, and wherein the efficiency of amplification, E, is similar for the plurality of standards and the target template; (b) measuring, at plural cycles of the amplifying regimen, signals from the target and each of the plurality of standard templates, wherein the measuring generates a set of measurements for each the template; (c) estimating a cycle threshold ($C_t$) value for each of the plurality of standard templates and the target template; (d) generating a standard curve, by plotting $C_t$ values estimated in step (c) on the y axis for each of the plurality of the standard templates versus the log of the known copy number on the x axis for each the standard template; and (e) calculating an initial concentration ($Q_0$) for the target nucleic acid template by solving the equation $C_{t(target)} = [I - \log(Q_0)]/\log(E)$ for $Q_0$, wherein I is the X intercept of the standard curve and E is the slope of the standard curve.

In one embodiment of this and other aspects described herein, the measurements of step (b) are entered into a computer-readable physical storage medium or memory, and steps (c)-(e) are performed by a computer processor executing instructions, encoded on a computer-readable physical storage medium or memory, for performing such steps. In particular embodiments, the computer-readable memory comprising the instructions can be the same as or different from the memory on which the measurements of step (b) are stored.

In another embodiment of this and other aspects described herein, $C_t$ is estimated by a method comprising the steps, for each set of measurements for each template: a) compiling a candidate list of all sets of consecutive signal measurements with cardinality 3 or greater; b) removing those points from the candidate list for which the area measurement is less than the area measurement at the previous cycle; c) computing a best-fitting line for each set of measurements, the line representing a log-linear amplification curve described by equation (1):

$$\log(\text{measured value}) = C_0 + E*C, \quad \text{[equation (1)]}$$

wherein C is the cycle number, $C_0$ is the X intercept and E is the slope of the line; d) removing candidate data sets having an R-squared correlation coefficient less than 0.8, a slope less than 1.45 or a slope greater than 2.1; e) computing a fitness score for each of the target nucleic acid and the plurality of standards; f) selecting the set with the highest fitness score as the best set for each of the target nucleic acid and the plurality of standards; and g) computing $C_t$ from the best set from each of the target nucleic acid and the plurality of standards, wherein $C_t$ is the fractional cycle number at the intercept of T(measured value) on the line described by equation (1).

In another embodiment of this and other aspects described herein, each of the standard templates and the target nucleic acid are amplified by the same pair of oligonucleotide primers.

In another embodiment of this and other aspects described herein, the measuring comprises measurement of a fluorescent signal.

In another embodiment of this and other aspects described herein, the measuring step (b) is performed on a plurality of aliquots taken from the reaction mixture at respective plural cycles during the amplifying regimen.

In another embodiment of this and other aspects described herein, prior to the measuring step, nucleic acid species in the plurality of aliquots are separated. The nucleic acid species can be separated, e.g., by capillary electrophoresis.

In another aspect, a computer-readable physical storage medium or memory is provided, the memory storing a program or set of instructions sufficient to implement a process, employing a computer, for determining an initial concentration ($Q_0$) of a target nucleic acid template. The template is present in a sample amplified in a nucleic acid amplification reaction regimen comprising a plurality of cycles of primer annealing, primer elongation and strand dissociation, and the reaction is performed using a reaction mixture comprising the target nucleic acid template and a plurality of standard templates, wherein each of the plurality of standard templates is present at a different, known copy number, and wherein the efficiency of amplification, E, is similar for the plurality of standards and the target template. The program stored in the memory comprises: a) instructions for inputting values for signals obtained from the target and each of the plurality of standard templates, at each of a plurality of cycles of the regimen, into the program; (b) instructions for estimating a cycle threshold ($C_t$) value for each of the plurality of standard templates and the target template using the values entered according to the instructions of (a); (c) instructions for generating a standard curve, by plotting $C_t$ values estimated in step (b) on the y axis for each of the plurality of the standard templates versus the log of the known copy number on the x axis for each the standard template; (d) instructions for calculating an initial concentration ($Q_0$) for the target nucleic acid template by solving the equation $C_{t(target)}=[I-\log(Q_0)]/\log(E)$ for $Q_0$, wherein I is the X intercept of the standard curve and E is the slope of the standard curve; and (e) instructions for outputting a calculated Qo for the target nucleic acid template to a memory, display or other user interface.

In another aspect, a computer system is provided for determining an initial concentration ($Q_0$) of a target nucleic acid template in a sample, the computer system comprising a computer processor, a physical memory or storage medium, a user interface and a display. The memory comprises a program or set of instructions sufficient to implement a process, employing the computer processor, for determining an initial concentration ($Q_0$) of a target nucleic acid template in a sample amplified in a nucleic acid amplification reaction regimen comprising a plurality of cycles of primer annealing, primer elongation and strand dissociation, wherein the reaction is performed using a reaction mixture comprising the target nucleic acid template and a plurality of standard templates, wherein each of the plurality of standard templates is present at a different, known copy number, and wherein the efficiency of amplification, E, is similar for the plurality of standards and the target template. The program on the memory comprises: a) instructions for inputting values for signals obtained from the target and each of the plurality of standard templates, at each of a plurality of cycles of the regimen, into the program; (b) instructions for estimating a cycle threshold ($C_t$) value for each of the plurality of standard templates and the target template using the values entered according to the instructions of (a); (c) instructions for generating a standard curve, by plotting $C_t$ values estimated in step (b) on the y axis for each of the plurality of the standard templates versus the log of the known copy number on the x axis for each standard template; (d) instructions for calculating an initial concentration ($Q_0$) for the target nucleic acid template by solving the equation $C_{t(target)}=[I-\log(Q_0)]/\log(E)$ for $Q_0$, wherein I is the X intercept of the standard curve and E is the slope of the standard curve; and (e) instructions for outputting a calculated $Q_0$ for the target nucleic acid template to a memory, display or other user interface.

BRIEF DESCRIPTION OF THE FIGURES

FIG. 1 shows a standard curve plot of cycle threshold (Ct) versus log of the concentration of reference target or calibrator target (Log 10 Concentration).

FIG. 2 shows the extension of the standard curve for low concentration templates by pairwise linear fit with low concentration reference calibrators.

FIG. 3 shows standard curves used to evaluate the efficiency of quantitative standards. Three separate reactions were examined with respect to the efficiency of the quantitative standard curve. These standard curves were used to quantify the unknown virus in the same reaction. In this example the delta efficiency can be shown by the equations: Eff sampleA–Eff sampleB, Eff sampleA–Eff sampleC, and EffsampleB–EffsampleC. The delta Eff is 0.05, 0.04, and 0.01 respectively. The slope, R2, and amplification efficiency are listed in the table.

FIGS. 4A-4C show the Log Log plots of copy number input and copy number derived over a linear range of target input. The copy number was estimated using the quantitative standards that are in each reaction. FIGS. 4A-4C show that the use of the quantitative standards is linear over a large dynamic range. The thick line in each figure is the fitted regression shown for comparison against the observations to judge goodness of fit. The two thin lines in each figure indicate the range around the fitted regression line likely to contain the population regression line.

The table and graph of FIG. 5 represent the Efficiency of each target in a reaction tube. The table and graph shows that in the same reaction tube the quantitative standards have the same efficiency as the target virus.

DETAILED DESCRIPTION

Multiplex PCR can permit detection and monitoring of the amplification of dozens of nucleic acid targets within the same reaction tube. Described herein are novel quantification methods that permit, within the context of increased multiplex capacity, the quantification of all targets within a single reaction tube. The methods are based on the amplification profile of internal calibration controls or standards utilizing at least two, but preferably three to five, nucleic acid templates that are amplified within the same reaction tube as the nucleic acid target(s) interrogated.

In one aspect of the methods described herein, each interrogated target and calibrator is labeled with a fluorophore, preferably 5,6-FAM, and identity of each is based on unique size. The concentration of the targets is preferably measured by capillary electrophoresis; however, other methods that monitor DNA concentration are also applicable. Quantification of the targets is based on amplification of calibrators within the same reaction in order to control for variability between reactions that may be due, for example, to contaminants introduced during sample preparation, environmental factors, and operator or instrument non-uniformity. In principle, similar quantification algorithms are applicable to real-time PCR methods given that a sufficient number of fluorophores are available that can be accurately monitored and quantified within the same reaction without significant overlap in spectra. In such an embodiment the calibrators should have unique (different from each other) sequences which would be targeted by the color-encoded probes. Accordingly, in such an embodiment there is no requirement for unique size for each calibrator.

In one embodiment, each calibration control is a DNA molecule which contains an amplifiable unique nucleotide sequence of varying length. The length must be unique for each calibrator with respect to all potentially amplified targets within the reaction. The amplified length of each calibrator is preferably within 250 bases of each other, but may differ in size up to 1000 bases. The amplifiable sequences of each calibrator are flanked by a set of sequences at their 5'- and 3'-ends that are used for priming PCR amplification. These sequences can be the same in all calibrators, or they can have different sequence, but common composition (defined as % CG content varying by no more than 10%) or similar melting temperatures (calculated using standard methods, such as next neighbor calculation and being within 5° C.). Importantly, the efficiency of PCR amplification using primers targeting selected sequences in calibrating molecules should be the same or similar (as used in this context, the efficiencies are "similar" if the difference in the amplification efficiency for all calibrators is less than 0.1). Calibrators are seeded in the reaction at minimally two, preferably three to five, concentrations ranging from 10-100,000 fold excess over the concentration of the least abundant calibrator. In the case when all calibrators are amplified by a common set of primers, the concentration of all calibrators is set such that the difference is no greater than 10,000-fold, preferably 100 to 1,000 fold to avoid competitive inhibition during PCR amplification. The concentration of calibrators is also dictated by variability of the assay such that the calculated copy number demonstrates a coefficient of variation between 0 and 50%, preferably <30%. It should be noted that where ranges are described herein, the ranges include and describe all integer values therebetween, as well as all sub-ranges, as if they were specifically recited herein. Thus, for example, the range 0 to 50% includes, not only 1%, 2%, 3%, 4% . . . 50%, but also, as non-limiting examples, 0-40%, 0-30%, 5-45%, 5-40%, 5-10%, 10-30%, and 40-45%.

In another embodiment the calibrators are RNA molecules. This is particularly useful if the target molecules being quantified are also RNAs. In this embodiment targets and calibrators are converted to DNA prior to PCR amplification using standard methods of reverse transcription known in art (for example RT transcription using random primers or target-specific primers).

In another embodiment the calibrators and targets to be quantified show amplification efficiencies within 0.1 of the calibrators. Then the assumption that amplification efficiency is the same for all calibrators and targets can be applied to simplify quantification algorithms as described below. Alternatively, the amplification efficiency of the targets can be different from amplification efficiency of the calibrators. In this case, a correction for calculation of targets' quantities can applied as also described below.

It is also well known that PCR amplification of very low level target results in poor amplification efficiencies. Additional algorithms are described herein to address quantification of these rare targets. Essentially, additional calibrators are seeded within the reaction at low levels, 5 to 100 copies per reaction. Targets amplifying with low efficiency, typically 1.4 to 1.6, are quantified to calibrators exhibiting amplification efficiencies within 0.1, preferably, 0.05 of the interrogated target. Low level calibrators exhibit the same characteristics as described for calibrators above Data Analysis Quantification of DNA fragment abundance is done through analysis of the label signal (preferably fluorescent signal) measurements modeled as amplification curves. Signal is measured after a plurality of cycles of an amplification regimen. In preferred embodiments the signal is measured in aliquots of amplification reaction mixture taken at a plurality of cycles of the amplification regimen. The signal for each different target and calibrator is measured at each measurement point (e.g., in each aliquot, the amount of signal corresponding to each target and each calibrator is measured, to provide a data set corresponding to the amplified amounts of each target and calibrator in the reaction mixture). The data analysis steps are:

1. Exponential Phase Identification;
2. Limit of Detection;
3. Standard Curve Quantification;
4. Low Concentration Quantification (alternative method); and
5. Efficiency Normalization.

Exponential Phase Identification

Exponential phase identification involves the following steps:

Step 1. Enumerate Candidate Point Sets

From a series of fluorescent measurements (RFU units) of increasing cycle number for each target, compile a candidate list of all sets of consecutive measurement points with cardinality 3 or greater.

Step 2. Remove Outliers

Remove internal points from each candidate set whenever the area measurement of a point is less than the area measurement at the previous cycle. Candidate sets of cardinality less than 3 are dropped from further consideration.

Step 3. Compute Linear Regression

Compute the best-fitting line for each set using linear regression. Use Log(RFU) and cycle number (C) for each point to create a log-linear amplification curve having equation:

$$\text{Log(RFU)} = C_0 + E_T * C \text{ where } C_0 \text{ is the intercept and } E_T \text{ is the slope of the line.} \quad \text{(Equation 1)}$$

Step 4. Remove Low Quality Sets

Disqualify candidate sets in which the R-squared correlation coefficient value is less than 0.80, the slope (E) is less than 1.45, or the slope is greater than 2.1. If no set passes this quality threshold, then the target is considered not present and reported as not amplified (not detected).

Step 5. Compute Fitness Score

The fitness of a candidate set is computed as a weighted sum of quality attributes. These attributes are (1) linearity (R-squared correlation coefficient), (2) number of data points used (cardinality), and (3) proximity to the fluorescence threshold. A set that is closer to the fluorescence threshold is considered higher quality because errors in the linear regression line cause an increase in $C_t$ estimation error that is proportional to distance.

Given a Log(RFU) threshold $T_{RFU}$, minimum log(RFU) value in the set $Min_{RFU}$, maximum Log(RFU) in the set $Max_{RFU}$, set cardinality Num, and correlation coefficient RSQ, compute the fitness score using Equation 2:

$$\text{Fitness Score} = \quad \text{(Equation 2)}$$

$$RSQ * 100 + \max(5, Num) * 1.0 + \text{if } Min_{RFU} \leq$$

$$T_{RFU} \leq Max_{RFU} \text{ then } 1.0$$

$$\text{else if } Max_{RFU} < T_{RFU} \text{ then } (T_{RFU} - Max_{RFU}) * -0.75$$

$$\text{else if } Min_{RFU} > T_{RFU} \text{ then } (Min_{RFU} - T_{RFU}) * -0.75$$

Step 6. Select Best Set

Select the set with the highest fitness score as the best set for the target.

Step 7. Compute Cycle Threshold

From the best set for each target, compute cycle threshold (Ct)) as the fractional cycle number at the intercept of $T_{RFU}$ on the regression line (defined by Equation 1).

Limit of Detection

Although poor quality amplification curves are identified in Step 4 of the Exponential Phase Identification method, additional acceptance criteria have been established through a comparison of the low-concentration samples and no template control samples (negatives). The supervised learning method of Decision Trees [1] is used to discriminate between these samples to establish limit of detection (LOD) criteria. The attributes used to assess quality are described in Table 1 and the inferred rules for determining when samples are not amplified are described in Table 2. If none of the failure criteria described in Table 2 are met, then the sample is considered to be detected (above LOD).

TABLE 1

Limit of Detection Attributes

| Attribute | Definition | Purpose |
|---|---|---|
| Maximum Peak Height | The maximum height of the target peak from any measurement | Assessment of maximum fragment abundance of the amplified target |
| Maximum Peak Area | The maximum area of the target peak from any measurement | Assessment of maximum fragment abundance of the amplified target |
| Peak Variance | Variance of the peak position in bases. | Assessment of the quality of target peak selection |
| Fitness Score | Amplification curve fitness score from Equation 2 | Assessment of amplification curve quality |

TABLE 2

Limit of Detection Algorithm

| Criteria | Explanation | Result |
|---|---|---|
| Criteria 1 | Maximum Peak Height <= 3313 | Failure: Low Peaks |
| Criteria 2 | Maximum Peak Height <= 7828 and Maximum Peak Height > 3313 and Peak Variance <= 0.538697 | Failure: High Variance |
| Criteria 3 | Maximum Peak Height >= 7828 and Peak Variance > 0.921343 and Fitness Score <= 20.649301 and Peak Area > 257247 | Failure: Low Quality |

Standard Curve Quantification—Method of Determining Nucleic Acid Template Quantities Using amplified reference targets of known concentration, a standard curve is created to estimate the initial concentration of other amplified targets.

For each reference target, the cycle threshold (Ct) is estimated using the Exponential Phase Identification method as described above. Each standard data point is obtained by associating Ct (plotted along the y-axis) with the initial template concentration (expressed as the log of the template copy number and plotted along the x-axis) (see FIGS. 1 and 3). Linear regression using the standard data points yields an approximation line that indicates a substantial degree of linearity in the standard curve. The linear relationship between Ct and initial concentration ($Q_0$) is described using Equation 3:

$Ct=[I-\log(Q_0)]/\log(E_R)$ where $I$ is the $x$ intercept and $E_R$ is the slope (efficiency)  (Equation 3)

Standard curve quality is assessed by evaluation of the r-squared value and the slope. The acceptable minimum value for r-squared is determined by modeling historical values using a Chi-squared distribution of $(1-R^2)$. Acceptable minimum and maximum values for the slope are modeled using a Gaussian distribution. These threshold values are set based on a 99.9% expected rate of acceptance in their respective distributions.

The cycle thresholds for measured targets are determined in the same manner as the reference targets using the Exponential Phase Identification method. The estimate of initial concentration of measured targets is determined using the standard curve described by Equation 3 which is rearranged in terms of $\log(Q_0)$ in Equation 4:

$\log(Q_0)=I-(Ct*\log(E_R))$  (Equation 4)

Low Concentration Quantification

Due to the gradual reduction in amplification efficiency at the end of a PCR reaction, the assumption of constant efficiency used by the standard curve model may no longer be valid. The use of extrapolation from the standard curve can therefore introduce measurement errors.

To correct for such changes in efficiency, the standard curve is extended with piecewise-linear segments using additional low concentration reference targets. These reference targets are not used in the linear regression that determines the original standard curve. The use of these targets for quantification is described in Equation 5 (and results are depicted, for example, in FIG. 2):

Let Ct be the cycle threshold of the measured target. (Equation 5)

Let $Ct-S_n$ be the cycle threshold of the smallest concentration reference target used in the standard curve.

Let $Ct-L_1, \ldots, Ct-L_n$ be the cycle thresholds of additional low concentration reference targets Initial concentration is estimated using linear interpolation or extrapolation (Equation 4)

Case 1: If $Ct \leq Ct-S_n$, then use previously defined standard curve method

Case 2: If $Ct-S_n < Ct \leq Ct-L_1$, then use linear interpolation using the line between calibrators $S_n$ and $L_1$ Case 3: If $Ct-L_i < Ct \leq Ct-L_{i+1}$, then use linear interpolation using the line between calibrators $L_i$ and $L_{i+1}$ Case 4: If $Ct > Ct-L_n$, then use linear extrapolation using the line between calibrators $L_n$ and $L_{n-1}$ Efficiency Variation Normalization In the simplest application of described quantification method it is assumed that the efficiency of the reference targets (calibrators) $E_R$ is identical to the efficiency of the measured target $E_T$ for all cycles in the reaction. For measurements in which the efficiency difference is greater than or equal to 0.1, a normalized estimate of initial concentration is computed using Equation 6:

$\log(Q_0)'=\log(Q_0)*(E_R/E_T)^{Ct}$ where $Ct$ is the cycle threshold of the measured target  (Equation 6)

whenever $|E_R-E_T| \geq 0.01$

For example, if $E_R=1.81$, $E_T=1.80$ and $Ct=32.0$, the normalized estimate would be $$\log(Q_0)' = \log(Q_0)*(1.81/1.80)^{32.0}$$ (Illustration 1)
$$= \log(Q_0)*1.194$$

A variety of methods can be used to estimate $E_R$, $E_T$, and $E_R/E_T$. For individual efficiency estimates, the slope of the linear region of the amplification curve can be used (e.g. by Exponential Phase Identification, the $E_T$ in Equation 1). The slope of a dilution (standard) curve from multiple concentrations of a target can also be used (e.g. by Standard Curve Quantification, the $E_R$ in Equation 3).

Efficiencies and efficiency ratios may be estimated using (1) only the targets measured in a single PCR reaction, (2) using historical measurements from many PCR reactions, or (3) using both historical measurements and measurements from a single reaction.

The methods described herein are illustrated by, but not intended to be limited by the following Example.

EXAMPLES

Example 1

The following conditions are used to amplify viral targets using quantitative standards in a multiplex PCR reaction. A PCR reaction is set up in a single tube containing the analyte, common PCR reagents (eg, DNA polymerase, dNTPs), and, for each target to be amplified, viral-specific primers where at least one of each pair is labeled with a fluorophore. The PCR reaction is assembled with three quantitative standards that are amplified from a single plant based gene using one primer pair for each of the quantitative standards in a competitive nature used to quantify the viral targets. The quantitative standards have similar amplification efficiencies to ensure accurate estimation of viral load of the unknown targets.

Template DNA was prepared by spiking plasma matrix with known copies of Cytomegalovirus (CMV), BK virus (BK), and Human Herpesvirus 7 (HHV7). The plasma was spiked with a dose of viral particles from 3e6 copies/ml to 3e2 copies/ml from three virus'; Cytomegalovirus (CMV), BK virus (BK), and Human Herpesvirus 7 (HHV7) to demonstrate linearity of the system. A sample processing control virus was added to the plasma to monitor that the extraction procedure. The nucleic acid was extracted from 400 ul of the spiked plasma samples with the use of the NucliSENS® easyMAG sample processing instrument and eluted in 25 ul of buffer. PCR reactions were set up to quantify the viral targets in the system. The PCR reaction contained; 1.) 2× Qiagen Multiplex PCR master mix, containing HotStarTaq DNA polymerase, Multiplex PCR Buffer, dNTP Mix 2.) 25× Multiplex primer mix, containing a) viral specific primers for each virus tested, primers for the amplification control, sample processing control, and quantification controls b) viral specific sensitivity controls and, quantification control targets. 3.) 20 ul of extracted sample.

The PCR reaction is placed in a MJ research PTC-200 thermocycler that is integrated with a PerkinElmer Multiprobe II Plus liquid handling system. The reaction is amplified under the following conditions: 1) 95°—15 minutes, 2) 95°—30 seconds, 62°—90 seconds, 72°—60 seconds—for 3 cycles 3) 95°—30 seconds, 60°—90 seconds, 72°—60 seconds—for 3 cycles 4) 95°—30 seconds, 58°—90 seconds, 72°—60 seconds—for 3 cycles 5) 95°—30 seconds, 57°—90 seconds, 72°—60 seconds—for 33 cycles. Starting at cycle 20, the thermocycler pauses and the lid opens to take a 2 ul aliquot of the PCR reaction and dispenses it into 13 ul formamide/rox standard mixture. The integrated thermocycler and liquid handler takes an aiquot of the PCR reaction from cycle 20 up to an including cycle 42. After all of the aliquots are taken the formamide rox mixture that now contains the PCR sample is placed at 95° C. for 5 minutes to denature the sample. The denatured samples are loaded into the Applied BioSystems 3730xl DNA Analyzer for analysis of each sample at each cycle taken.

The samples are analyzed to determine the initial concentration of a nucleic acid as outlined in "Method of Determining Nucleic Acid Template Quantities" section of this disclosure.

TABLE 3

Summary of STAR multiplex primer sequence

| Primer | Primer Sequence |
|---|---|
| Rubisco Forward | 5'-CTT TGT CGG GTT TTC TCC GTA TCC-3' (SEQ ID NO: 1) |
| Rubisco Reverse | 5'-/56-FAM/TTC GCT CGT AGT CGA ACG CC-3' (SEQ ID NO: 2) |
| CMV Forward | 5'-/56-FAM/TCC GGC GAT GTT TAC TTT ATC AAC C-3' (SEQ ID NO: 3) |
| CMV Reverse | 5'-CCG TGA TAA AAC ACA AAC TGG CAA A-3' (SEQ ID NO: 4) |
| HHV7 Forward | 5'-/56-FAM/ATA TTG TGC CTT GCA GCT CTA TGT TTC TC-3' (SEQ ID NO: 5) |
| HHV7 Reverse | 5'-ACC GAG ATG CGG CTT TTA TAG TTG A-3' (SEQ ID NO: 6) |
| BK Forward | 5'-/56-FAM/GCT TGA TCC ATG TCC AGA GTC TTC A-3' (SEQ ID NO: 7) |
| BK Reverse | 5'-GGA AGG AAA GGC TGG ATT CTG AGA T-3' (SEQ ID NO: 8) |
| Sample ctrl Forward | 5'-/56-FAM/TGC TTT TGT AAT TGG CTT CTG ACC A-3' (SEQ ID NO: 9) |
| Sample ctrl Reverse | 5'-CGC AAT CCA ATA ACT TGG AAC GAA T-3' (SEQ ID NO: 10) |

TABLE 4

Summary of Quantitative Standards Amplified Region

| Standard | Amplified Region |
|---|---|
| DNA2 | 5'-CGTCGGGTTTTCTCCGTATCCCGTCAATTCAAAAGTCTCAAAACCCTTCCTTT CTCTTTTCTCGACCCAAGAAATCTTTGGTGAGACCCATTTCAGCTTCAAGCTCAGAGT TGC-3' (SEQ ID NO: 11) |
| DNAB | 5'- GTCGTATCCGGGAAGTCTGTGGCAGAACCTGCGGTGGTACCGGAAGGT TTGGGACTTGTAGCCAGGCGTGATATTGGAAGAAACGAGGTCGTATTG GAGATTCCCAAGCGATTGTGGATAAACCCAGAGACAGTGACTGCTTCC |

TABLE 4-continued

Summary of Quantitative Standards Amplified Region

| Standard | Amplified Region |
|---|---|
| | AAGATTGGACCTTTATGCGGCGGATTAAAGCCGTGGGTTTCAGTAGCT |
| | CTGTTTTTGATCAGAGAGAAGTATGAAGAAGAGTCTTCATGGAGAGTT |
| | TATCTTGATATGCTTCCTCAATCTACTGATTCTA (SEQ ID NO: 12) |
| DNAC | 5'-TCTACTGATTCTACTGTCTTCTGGTCAGAAGAGGAGCTT |
| | GCTGAGCTTAAAGGGACTCAACTGTTGAGCACCACATTGGGTGTGAAA |
| | GAGTATGTGGAGAATGAATTCTTGAAACTGGA |
| | ACAAGAGATATTACTGCCTAACAAAGATCTCTTCTCATCCCGCATAAC |
| | ACTTGATGACTTCATATGGGCGTTTGGGATCC |
| | TCAAGTCGAGGGCTTTTTCTCGTCTCCGTGGCCAAAACCTTGTCTTGAT |
| | CCCTCTTGCAGACTTGATAAACCATAACCCC |
| | GCGATAAAGACAGAAGATTATGCATACGA-3' (SEQ ID NO: 13) |

As is apparent to one of skill in the art, various modification and variations of the above embodiments can be made without departing from the spirit and scope of this invention. These modifications and variations are within the scope of this invention.

The invention claimed is:

1. A method of determining an initial concentration ($Q_0$) of a target nucleic acid template in a sample, the method comprising the steps of:

a) amplifying said target nucleic acid template and a plurality of standard templates, each of said standard templates present at a different, known copy number, in a nucleic acid amplification reaction regimen comprising a plurality of cycles of primer annealing, primer elongation and strand dissociation, wherein said reaction is performed using a reaction mixture comprising said target nucleic acid template and said plurality of standard templates, and wherein the efficiency of amplification, E, is similar for said plurality of standards and said target template;

b) measuring, at plural cycles of said amplifying regimen, fluorescent signals from said target and each of said plurality of standard templates after nucleic acid species in an aliquot taken from the reaction mixture are separated by capillary electrophoresis, wherein said measuring generates a set of measurements for each said template;

c) estimating a cycle threshold ($C_t$) value for each of said plurality of standard templates and said target template, wherein the $C_t$ value is estimated by a method comprising the steps, for each set of measurements for each said template, of:
  i) compiling a candidate list of all sets of consecutive signal measurements with cardinality 3 or greater;
  ii) removing those signal measurements from said candidate list for which peak area measurement is less than peak area measurement at the previous cycle;
  iii) computing a best-fitting line by linear regression for each set of measurements, said line representing a log-linear amplification curve described by equation (1):

$$\log(\text{measured value}) = C_0 + EC$$

wherein C is the cycle number, $C_0$ is the X intercept and E is the slope of the line;
  iv) computing a fitness score for each of said target nucleic acid and said plurality of standards, wherein the fitness score is computed as a weighted sum of the correlation coefficient of the linear regression computed in step (iii), the cardinality of the candidate data set, and proximity to the fluorescence threshold;
  v) selecting the set with the highest fitness score as the best set for each of said target nucleic acid and said plurality of standards; and
  vi) computing $C_t$ from the best set from each of said target nucleic acid and said plurality of standards, wherein $C_t$ is computed by:
    A) choosing a threshold value for log(measured value) of equation (1)
    B) solving equation (1) for C when log(measured value) equals the chosen threshold value, $C_0$ equals the X intercept determined in step (c)(iii) and E equals the slope determined in step (c)(iii);
    C) setting $C_t$ equal to the solved value of C;

d) generating a standard curve by plotting $C_t$ values estimated in step (c) on the y axis for each of said plurality of said standard templates versus the log of said known copy number on the x axis for each said standard template; and e) calculating an initial concentration ($Q_0$) for said target nucleic acid template by solving the equation $$C_{t(target)} = \frac{[I - \log(Q_0)]}{\log(E_R)}$$

for $Q_0$, wherein I is the X intercept of said standard curve and $E_R$ is the efficiency obtained from said standard curve.

2. The method of claim 1 wherein said measurements of step (b) are entered into a computer-readable physical memory, and wherein steps (c)-(e) are performed by a computer processor executing instructions, encoded on a computer-readable physical memory, for performing such steps.

3. The method of claim 1 wherein each of said standard templates and said target nucleic acid are amplified by the same pair of oligonucleotide primers.

4. The method of claim 1 wherein said measuring step (b) is performed on a plurality of aliquots taken from said reaction mixture at respective plural cycles during said amplifying regimen.

5. A non-transitory computer-readable physical storage medium comprising instructions, that when executed by a processor, cause the processor to perform a procedure comprising the steps of:

a) receiving a plurality of measurements obtained from a plurality of standard templates;

b) receiving a plurality of measurements obtained from a target template;

c) estimating a cycle threshold (CO value for each of said plurality of standard templates and said target template, wherein the $C_t$ value is estimated by a method comprising the steps, for each set of measurements for each said template, of:
  i) compiling a candidate list of all sets of consecutive signal measurements with cardinality 3 or greater;
  ii) removing those signal measurements from said candidate list for which peak area measurement is less than peak area measurement at the previous cycle;
  iii) computing a best-fitting line by linear regression for each set of measurements, said line representing a log-linear amplification curve described by equation (1):

$$\log(\text{measured value}) = C_0 + EC$$

wherein C is the cycle number, $C_0$ is the X intercept and E is the slope of the line;
  iv) computing a fitness score for each of said target nucleic acid and said plurality of standards, wherein the fitness score is computed as a weighted sum of the correlation coefficient of the regression computed in step (iii), the cardinality of the candidate data set, and proximity to the fluorescence threshold;
  v) selecting the set with the highest fitness score as the best set for each of said target nucleic acid and said plurality of standards; and
  vi) computing $C_t$ from the best set from each of said target nucleic acid and said plurality of standards, wherein $C_t$ is computed by:
    A) choosing a threshold value for log(measured value) of equation (1)
    B) solving equation (1) for C when log(measured value) equals the chosen threshold value, $C_0$ equals the X intercept determined in step (c)(iii) and E equals the slope determined in step (c)(iii);
    C) setting $C_t$ equal to the solved value of C;

d) generating a standard curve by plotting $C_t$ values estimated in step (c) on the y axis for each of said plurality of said standard templates versus the log of said known copy number on the x axis for each said standard template; and e) calculating an initial concentration ($Q_0$) for said target nucleic acid template by solving the equation $$C_{t(target)} = \frac{[I - \log(Q_0)]}{\log(E_R)}$$

for $Q_0$, wherein I is the X intercept of said standard curve and $E_R$ is the efficiency obtained from said standard curve.

6. A system comprising a computer processor, and instructions that cause the processor to perform a procedure comprising the steps of:
   a) receiving a plurality of measurements obtained from a plurality of standard templates;
   b) receiving a plurality of measurements obtained from a target template;
   c) estimating a cycle threshold ($C_t$) value for each of said plurality of standard templates and said target template, wherein the $C_t$ value is estimated by a method comprising the steps, for each set of measurements for each said template, of:
      i) compiling a candidate list of all sets of consecutive signal measurements with cardinality 3 or greater;
      ii) removing those signal measurements from said candidate list for which peak area measurement is less than peak area measurement at the previous cycle;
      iii) computing a best-fitting line by linear regression for each set of measurements, said line representing a log-linear amplification curve described by equation (1):

$$\log(\text{measured value}) = C_0 + EC$$

wherein C is the cycle number, $C_0$ is the X intercept and E is the slope of the line;
      iv) computing a fitness score for each of said target nucleic acid and said plurality of standards, wherein the fitness score is computed as a weighted sum of the correlation coefficient of the regression computed in step (iii), the cardinality of the candidate data set, and proximity to the fluorescence threshold;
      v) selecting the set with the highest fitness score as the best set for each of said target nucleic acid and said plurality of standards; and
      vi) computing $C_t$ from the best set from each of said target nucleic acid and said plurality of standards, wherein $C_t$ is computed by:
         A) choosing a threshold value for log(measured value) of equation (1)
         B) solving equation (1) for C when log(measured value) equals the chosen threshold value, $C_0$ equals the X intercept determined in step (c)(iii) and E equals the slope determined in step (c)(iii);
         C) setting $C_t$ equal to the solved value of C;
   d) generating a standard curve by plotting $C_t$ values estimated in step (c) on the y axis for each of said plurality of said standard templates versus the log of said known copy number on the x axis for each said standard template; and
   e) calculating an initial concentration ($Q_0$) for said target nucleic acid template by solving the equation $$C_{t(target)} = \frac{[I - \log(Q_0)]}{\log(E_R)}$$

for $Q_0$, wherein I is the X intercept of said standard curve and $E_R$ is the efficiency obtained from said standard curve.

* * * * *

SEQUENCE LISTING

<160> NUMBER OF SEQ ID NOS: 13

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctttgtcggg ttttctccgt atcc                                         24

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttcgctcgta gtcgaacgcc                                              20

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tccggcgatg tttactttat caacc                                        25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccgtgataaa acacaaactg gcaaa                                         25

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atattgtgcc ttgcagctct atgtttctc                                     29

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
accgagatgc ggcttttata gttga                                         25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcttgatcca tgtccagagt cttca                                         25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggaaggaaag gctggattct gagat                                         25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgcttttgta attggcttct gacca                                         25

-continued

```
<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgcaatccaa taacttggaa cgaat                                           25

<210> SEQ ID NO 11
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
cgtcgggttt tctccgtatc ccgtcaattc aaaagtctca aaacccttcc tttctctttt     60
ctcgacccaa gaaatctttg gtgagaccca tttcagcttc aagctcagag ttgc          114

<210> SEQ ID NO 12
<211> LENGTH: 274
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gtcgtatccg ggaagtctgt ggcagaacct gcggtggtac cggaaggttt gggacttgta     60
gccaggcgtg atattggaag aaacgaggtc gtattggaga ttcccaagcg attgtggata   120
aacccagaga cagtgactgc ttccaagatt ggacctttat gcggcggatt aaagccgtgg   180
gtttcagtag ctctgttttt gatcagagag aagtatgaag aagagtcttc atggagagtt   240
tatcttgata tgcttcctca atctactgat tcta                               274

<210> SEQ ID NO 13
<211> LENGTH: 308
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
tctactgatt ctactgtctt ctggtcagaa gaggagcttg ctgagcttaa agggactcaa     60
ctgttgagca ccacattggg tgtgaaagag tatgtggaga atgaattctt gaaactggaa   120
caagagatat tactgcctaa caaagatctc ttctcatccc gcataacact tgatgacttc   180
atatgggcgt ttgggatcct caagtcgagg gcttttctc gtctccgtgg ccaaaacctt    240
gtcttgatcc ctcttgcaga cttgataaac cataaccccg cgataaagac agaagattat   300
gcatacga                                                            308
```